United States Patent [19]

Loder, Jr. et al.

[11] 3,976,440

[45] Aug. 24, 1976

[54] NON-LEADED GASOLINE HAVING IMPROVED ANTI-KNOCK QUALITY

[75] Inventors: Wallace R. Loder, Jr., North Olmsted; Philip S. Fay, Lyndhurst; Franklin Veatch, University Heights, all of Ohio

[73] Assignee: Standard Oil Company, Cleveland, Ohio

[22] Filed: Sept. 24, 1975

[21] Appl. No.: 616,388

[52] U.S. Cl. .................................. 44/68; 260/429 R; 260/439 R; 260/438.1; 260/429.9; 260/429 K
[51] Int. Cl.² ............................................ C10L 1/24
[58] Field of Search ......... 44/68; 260/429 R, 439 R, 260/438.1, 429.9, 429 K

[56] References Cited

UNITED STATES PATENTS

| | | | |
|---|---|---|---|
| 2,777,874 | 1/1957 | Asseff et al. | 260/429 X |
| 3,794,473 | 2/1974 | Eisentraut et al. | 44/68 |
| 3,880,900 | 4/1975 | Fujii et al. | 260/429 K |

*Primary Examiner*—Daniel E. Wyman
*Assistant Examiner*—Y. Harris-Smith
*Attorney, Agent, or Firm*—John F. Jones; Sherman J. Kemmer

[57] ABSTRACT

Non-leaded motor fuel compositions having improved octane rating contain O-alkyldiselenocarbonates of certain metals as octane improvers.

7 Claims, No Drawings

NON-LEADED GASOLINE HAVING IMPROVED ANTI-KNOCK QUALITY

This invention relates to improved hydrocarbon fuel compositions and more particularly pertains to improved non-leaded motor gasoline fuel compositions having improved octane numbers.

Recent automotive design trends have been toward engines having greater power for the same size engine and more efficient utilization of the gasoline fuel. Environmental considerations have resulted in legislation setting limits on the amounts and types of auto exhaust emissions. The requirements for catalytic mufflers in auto exhaust systems have necessitated the adoption of non-leaded gasoline which in turn has created a need for non-lead octane improvers for the production of acceptable lead-free gasoline.

We have discovered that O-alkyldiselenocarbonates of certain transition metals are gasoline-soluble and function as effective anti-knock agents in non-leaded gasoline. These useful anti-knock compounds generally conform to the structure

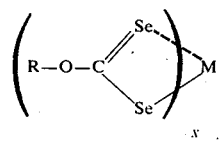

wherein M is a metal preferably manganese, iron, nickel, copper or zinc, X is the valence state of the metal and R is an alkyl, cycloalkyl or aryl group.

Generally, the O-alkyldiselenocarbonates of this invention can be prepared by reaction of carbon diselenide, an aliphatic alcohol and a metal salt. In general, the longer the alkyl chain in the alcohol used, the lower the melting point and the higher the fuel solubility will be for the particular O-alkyldiselenocarbonates.

A useful concentration range for the octane improvers of this invention is from 0.0625 to 1.00 grams (of metal) per gallon of gasoline. The octane response to a given additive, of course, is dependent on the octane level of the base fuel.

The base gasoline stock useful as a fuel in this invention can comprise a mixture of hydrocarbons boiling in the gasoline range and can be either a straight-run gasoline or a gasoline obtained from a conventional cracking process, or mixtures thereof. The base gasoline may also contain components from various other refinery processes, such as alkylation, isomerization, hydrogenation, polymerization, catalytic reforming, or combinations of two or more of such processes.

It is intended that the motor fuel of this invention may also include other known additives for commercial fuels, such as detergents, oxidation inhibitors, gum inhibitors, deicers, dyes, solvent oils, and the like.

In order to determine the effect of the O-alkyldiselenocarbonates on the octane rating of the unleaded motor fuel, blended fuels were evaluated in the standard ASTM (research) and ASTM (motor) octane test procedures.

The following examples will further illustrate the invention.

EXAMPLE A

The O-alkyldiselenocarbonates were prepared in the following manner:

Into a three-neck 250-ml. round-bottom flask equipped with magnetic stirrer, nitrogen outlet, thermometer, pressure equalizing addition funnel with nitrogen inlet were placed 25 ml. of n-pentyl alcohol and 1.9 grams of 87% KOH pellets. A moderate nitrogen flow was maintained and the flask was cooled to $-10°C$ by means of a dry ice-acetone bath. To this vigorously stirred cold solution was added over 1 hour 4.2 grams (0.025 mole) of carbon diselenide in 40 ml. of p-dioxane. A yellow-orange precipitate soon formed. At the completion of the addition, the mixture was stirred an additional 15 minutes without cooling. The flask was then filled with diethyl ether and the contents were filtered. The yellow precipitate of the yellow potassium diselenocarbonate was washed with ether and was dissolved in 25 ml. of distilled water and cooled to 0°C. This cooled solution was then added to a stirred mixture of a metal salt (i.e., $FeCl_3$ or $NiCl_2$) (in 20% excess) in 25 ml. of distilled water and 150 ml. of benzene at 5°C. After 10 minutes of stirring, the mixture was filtered. The benzene layer was then separated, washed twice with 50-ml. portions of distilled water, and dried about 3 hours over $Na_2SO_4$. The mixture was filtered and the benzene was evaporated leaving a viscous oil (or a solid in the case of nickel). The oil was dried under 50–100 microns of vacuum at 35°C for 4 hours. Table 1 lists the O-pentyldiselenocarbonate metal chelates prepared in this manner.

Table 1

| Compound | % Metal | % Se | Color | M. P. |
|---|---|---|---|---|
| tris(O-pentyldiseleno-carbonato) manganese III | 6.65 | 57.35 | red-brown | oil |
| tris(O-pentyldiseleno-carbonato) iron III | 6.75 | 57.28 | brown | oil |
| bis(O-pentyldiseleno-carbonato) nickel II | 10.25 | 55.14 | purple plates | 91°C |
| bis(O-pentyldiseleno-carbonato) copper II | 11.00 | 54.67 | black-purple | oil |
| bis(O-pentyldiseleno-carbonato) zinc II | 11.28 | 54.50 | yellow-orange | oil |

EXAMPLE B

The physical and chemical properties of the base fuel employed in the octane test program were as follows:

| distillation | °F |
|---|---|
| initial B. P. | 90 |
| 10% | 127 |
| 50% | 236 |
| 90% | 334 |
| E. P. | 406 |
| percent recovered | 95 |
| percent residue | 1 |
| percent loss | 4 |
| gravity, °API | 56.5 |
| RVP, psig | 9.3 |
| octane ASTM research | 93.2 |
| octane ASTM motor | 85.2 |
| composition | |
| light cat. dist. | 15% |
| light cat. ref. | 5% |
| heavy cat. ref. | 15% |
| total cat. ref. | 32% |
| light isocrackate | 22% |
| motor alkylate | 11% |
| FIA, % aromatic | 27.2 |
| % olefins | 2.4 |

-continued

% saturates 70.4

Table 2 shows the results of using varying amounts of the metal chelates described in Example A in the base fuel.

Table 2

| Example | Metal Chelate | Conc. Grams Metal/ Gallon | Change in Octane Number Over Base Fuel | |
|---|---|---|---|---|
| | | | Research Octane Number | Motor Octane Number |
| 1 | manganese III | 0.0625 | 0.1 | −0.2 |
| 2 | manganese III | 0.125 | 0.4 | 0.0 |
| 3 | manganese III | 0.250 | 0.9 | 0.6 |
| 4 | manganese III | 0.50 | 1.9 | 1.4 |
| 5 | manganese III | 1.00 | 4.1 | 4.0 |
| 6 | iron III | 0.0625 | 0.0 | 0.1 |
| 7 | iron III | 0.125 | 0.2 | 0.2 |
| 8 | iron III | 0.250 | 0.6 | 0.5 |
| 9 | iron III | 0.500 | 1.2 | 1.2 |
| 10 | iron III | 1.000 | 1.8 | 1.9 |
| 11 | nickel II | 0.0625 | 0.4 | 0.3 |
| 12 | nickel II | 0.125 | 0.7 | 0.7 |
| 13 | nickel II | 0.250 | 1.0 | 1.0 |
| 14 | nickel II | 0.500 | 1.4 | 1.7 |
| 15 | copper II | 0.0625 | 0.0 | 0.0 |
| 16 | copper II | 0.125 | 0.1 | 0.3 |
| 17 | copper II | 0.250 | 0.3 | 0.4 |
| 18 | copper II | 0.500 | 0.8 | 1.0 |
| 19 | copper II | 1.000 | 1.8 | 2.3 |
| 20 | zinc II | 0.0625 | 0.0 | 0.2 |
| 21 | zinc II | 0.125 | 0.2 | −0.1 |
| 22 | zinc II | 0.250 | 0.6 | 0.3 |
| 23 | zinc II | 0.500 | 1.0 | 0.8 |
| 24 | zinc II | 1.000 | 2.0 | 1.8 |

We claim:

1. A non-leaded gasoline composition for internal combustion engines containing from about 0.0625 to 1.00 grams of metal per gallon of fuel of a compound having the formula $$\left( R-O-C \underset{Se}{\overset{Se}{\diagdown}} \right)_x M-$$

wherein M is a metal selected from the group consisting of manganese, iron, nickel, copper and zinc, X is the valence state of the metal and R is an alkyl, cycloalkyl or aryl group.

2. The motor fuel composition of claim 1 wherein R is an alkyl group.

3. The motor fuel composition of claim 2 wherein the compound is tris(O-pentyldiselenocarbonato) manganese III.

4. The motor fuel composition of claim 2 wherein the compound is tris(O-pentyldiselenocarbonato) iron III.

5. The motor fuel composition of claim 2 wherein the compound is bis(O-pentyldiselenocarbonato) copper II.

6. The motor fuel composition of claim 2 wherein the compound is bis(O-pentyldiselenocarbonato) nickel II.

7. The motor fuel composition of claim 2 wherein the compound is bis(O-pentyldiselenocarbonato) zinc II.

* * * * *